United States Patent [19]

Taufen

[11] 4,377,640

[45] Mar. 22, 1983

[54] SULPHUR GAS GEOCHEMICAL PROSPECTING

[75] Inventor: Paul M. Taufen, Golden, Colo.

[73] Assignee: Texasgulf Inc., Stamford, Conn.

[21] Appl. No.: 265,644

[22] Filed: May 20, 1981

[51] Int. Cl.$^3$ .................... G01N 33/24; G01N 31/08; G01N 21/72

[52] U.S. Cl. ..................................... 436/32; 436/123; 436/161; 436/171

[58] Field of Search .............. 23/230 EP; 436/31, 32, 436/123, 161, 171

[56] References Cited

U.S. PATENT DOCUMENTS

| | | | |
|---|---|---|---|
| 2,348,103 | 5/1944 | Beckman | 23/230 EP |
| 2,370,793 | 3/1945 | Horvitz | 23/230 EP |
| 2,617,296 | 11/1952 | Wisenbaker | 23/230 EP |
| 3,302,706 | 2/1967 | Thompson | 23/230 EP |
| 3,692,481 | 9/1972 | Mitchell | 422/54 |
| 3,702,235 | 11/1972 | Fallgatter | 23/230 EP |
| 4,213,763 | 7/1980 | Madec | 23/230 EP |

OTHER PUBLICATIONS

Rouse, G. E. and Stevens, D. N. 1971; The Use of Sulfur Dioxide Gas Geochemistry in the Detection of Sulfide Deposits.

Journal of Geochemical Exploration, Jun., 1978, Hinkle, M. E. and Kantor, J. A., Collection and Analysis of Soil Gases Emanating from Buried Sulfide Mineralization.

Rose, A. W., Hawks, H. E. and Webb, J. S., Geochemistry in Mineral Exploration, Second Edition, Academic Press.

*Primary Examiner*—Michael S. Marcus
*Attorney, Agent, or Firm*—Denis A. Polyn

[57] ABSTRACT

A method of geochemical prospecting for buried sulphur mineralization which comprises collecting relatively organic free soil samples, desorbing bound sulphur gases from the soil samples, and analyzing the sulphur gases.

12 Claims, No Drawings

SULPHUR GAS GEOCHEMICAL PROSPECTING

BACKGROUND OF THE INVENTION

1. Field of the Invention

This invention relates to a method of geochemical prospecting for buried sulphur and sulphide mineralization, and, more particularly, to a method of collecting and analyzing soil samples to determine the presence of buried sulphur and sulphide mineralization.

2. Description of the Prior Art

The field of sulphur gas geochemical prospecting is dominated by procedures recommending the use of interstitial soil gas as a sampling medium whether the measure gas is collected over a short or over a long period of time. Rouse, G. E. and Stevens, D. N. 1971, The Use Of Sulfur Dioxide Gas Geochemistry In The Detection Of Sulfide Deposits; Journal Of Geochemical Exploration, June, 1978, Hinkle, M. E. and Kantor, J. A., Collection And Analysis Of Soil Gases Emanating From Buried Sulfide Mineralization. When a solid natural substrate is mentioned in the literature as a sample type in a sulphur gas geochemical survey, the indication is that soil and humus are effective accumulators of sulphur gases derived from buried sulphur gas producing ore deposits. Rose, A. W. Hawks, H. E. and Webb, J. S., Geochemistry In Mineral Exploration, Second Edition, Academic Press.

There is nothing in the prior art which indicates that natural degradation of plant and organic matter causes a significant interference in sulphur gas prospecting surveys in the generation of the same naturally stable sulphur gases emitted by buried mineral deposits. There is also nothing in the prior art which indicates that soil depth is critical in establishing informative anomaly patterns in sulphur gas geochemical prospecting. In fact, the published literature recommending humus and interstitial soil gas as sample types (Geochemistry In Mineral Exploration, ibid) has probably served more to hinder than to help the sulphur gas geochemistry prospector. Geochemistry In Mineral Exploration, Ibid.

SUMMARY OF THE INVENTION

It is an object of the present invention to describe a method of geochemical prospecting for buried sulphur mineralization.

A further object of the invention is to describe a method of collecting and analyzing soil samples to determine the presence of buried sulphur mineralization.

These and other objects are achieved by the provision of a method of geochemical prospecting for buried sulphur mineralization which comprises:
 (a) collecting at least one soil sample from a depth beneath the zone of high plant and organic matter contribution to the composite soil;
 (b) desorbing bound sulphur gases from said soil sample; and,
 (c) analyzing said sulphur gases to determine the presence of buried sulphur mineralization.

DETAILED DESCRIPTION OF THE INVENTION

I have discovered that proper collection and handling of soil samples for sulphur gas analysis is critical in establishing good anomaly contrast between samples directly overlying buried mineralization and samples distant from buried orebodies. For example, at the Union Sulphur Deposit in west Texas, I have observed a direct relationship between soil sulphur gas enrichment and proximity to buried sulphur mineralization with soils overlying ore enriched up to one hundred fold versus background soils. At this location, soil sampling depth was discovered to be critical in determining adsorbed sulphur gas patterns related to mineralization. I discovered, through the use of sulphur gas chromatograms, the importance of collecting soil samples beneath the upper soil horizons where decaying plant and organic matter contribute heavily to the composite soil. A series of soil samples containing plant material were discovered to have a set of sharp sulphur gas peaks in their chromatograms similar to those found in a series of soil samples taken over the Union Sulphur Deposit from beneath the organic layer. The analyzed soil samples containing plant material were comprised of decaying organic matter and surface soil found well removed from any buried sulphur mineralization. A comparison of the chromatograms of the soil samples containing plant material with soil samples taken from beneath the organic layer indicates that the same sulphur gas species (e.g. hydrogen sulphide, carbonyl sulphide, methyl mercaptan, carbon disulphide, 2-methyl-2-propyl-thiol, and dimethyl disulphide) are found in both types of soil samples. The foregoing clearly indicates that decaying plant and organic matter produces some of the same sulphur gases emitted by buried sulphur mineralization and that soils containing significant quantities of those materials (i.e. near surface soils) are an inappropriate sample type for sulphur gas geochemical prospecting. I have discovered that only soil samples collected at a depth beneath the zone of high plant-organic matter contribution are capable of clearly reflecting buried sulphur gas sources.

I have determined that soil sample gas concentrations can accurately indicate buried mineralization when soil samples are handled according to the following procedure. Soil samples are sieved, preferably through an 80-mesh screen, and placed in dark, airtight jars, preferably glass, which are sealed against outside air and light. Soil samples inside the jars are immediately refrigerated, preferably at a temperature below 25° C., and maintained in that state until analysis.

I have discovered that analyzing sulphur gases bound to soils, as opposed to prior art techniques which utilized interstitial soil gas as a sampling medium, yields a "time averaged" gas analysis since free sulphur gases in soil interstices equilibrate with adsorption or absorption sites on soils. This "time averaged" soil analysis is an improvement over uncombined gas analysis since gases held in soils are far less subject to barometric pressure and temperature changes which can strongly affect free gas (i.e. interstitial soil gas) concentration levels.

The method of the present invention is further illustrated in the following non-limiting example.

EXAMPLE

Soil samples over three case study areas (i.e. Union Sulphur Deposit, Maverick Draw Deposit, and Saddle Butte Deposit) in west Texas were collected using an air rotary hydraulically operated Winkie drill with a small bi-cone bit. Cuttings from the 9' to 11' drilling interval were collected and sieved through an 80-mesh (180 $\mu$m) screen in the field. The minus 80-mesh fraction was placed in a quart-sized mason jar wrapped in aluminum foil to keep stray light from the soil sample and the jar was placed in a refrigerated cooler (sulphur gas compounds are subject to degradation by light and by microbial activity). Physical descriptions, mineralogical descriptions and degree of effervescence with dilute hydrochloric acid were recorded for each sample. Coolers and mason jars were shipped to the University of Idaho laboratory where they arrived with the jars and soil samples below room temperature.

Statistical control in each survey consisted of monitoring sulphur gas concentration differences due to sampling error and sulphur gas concentration differences due to analytical error according to a prescribed method. See, for example, Miesch, A. T. et al; Geochemical Survey of Missouri - Methods of Sampling Laboratory Analysis, and Statistical Reduction of Data, U.S.G.S. Professional Paper 954-A. Sampling error was examined by collecting three soils (from three separate drill holes) within randomly selected sample sites along a profile. Comparison of analysis values from the three samples gave an indication of the error associated with sampling one soil within a sample site. Sulphur gas concentrations from three samples within a site were plotted in the profile diagrams at all sites where sampling error was monitored. Sampling error was generally about ±3 nanograms (3 billionths of a gram) with the exception of much greater sampling error of the 0 profile point at the Union Deposit where much greater variation was seen in the acid vs. alkaline soils from within the sample site. Analytical error was examined by running duplicate sulphur gas analyses on selected samples. For sulphur gas concentrations less than 5 nanograms, analytical error associated with each analysis was about ±2 nanograms. Analytical error associated with sulphur gas levels above 5 nanograms was about ±15%.

Analyses at the University of Idaho were run by gas chromatography using preconcentration at liquid oxygen temperature and by a total sulphur gas method using a temperature dependent solid substrate preconcentrator. Both methods employ a sulphur specific flame photometric detector in analysis of the preconcentrated gases. The general scheme of determining adsorbed sulphur gas content of the preserved soils includes desorption of sulphur gases from soils by heating, concentration of the desorbed gases in a cold trap or on a solid concentrator, and injection of the concentrated gases into a sulphur analyzer (flame photometric detector). The gas chromatography techniques used were developed at the University of Idaho; Farwell, S. W. and Gluck, S., Determination of Sulphur Containing Gases by a Deactivated Cryogenic Enrichment and Capillary Gas Chromatographic System, Anal. Chem., 51 (1979).

I claim:

1. A method of geochemical prospecting for buried sulphur mineralization which comprises:
    (a) collecting a plurality of soil samples selected only from a depth beneath the zone of high plant and organic matter contribution to the composite soil and placing each said soil sample in a dark, airtight container;
    (b) desorbing all bound sulphur gases from each said soil sample solely by heating each said soil sample;
    (c) analyzing said sulphur gases to determine the presence of buried sulphur mineralization.

2. A method according to claim 1, wherein said buried sulphur mineralization is sulphur ore.

3. A method according to claims 1 and 2, wherein said buried sulphur mineralization is located in a tropical or temperate environment.

4. A method according to claim 1, wherein each said soil sample is collected at a depth beneath any plant and organic matter contribution to the composite soil.

5. A method according to claim 1, wherein each said soil sample is refrigerated until it is to be analyzed.

6. A method according to claim 1, wherein said buried sulphur mineralization is a sulphide deposit.

7. A method according to claim 1, wherein analyzing said sulphur gases to determine the presence of buried sulphur mineralization is accomplished by a total sulphur gas method.

8. A method according to claim 7, wherein said total sulphur gas method involves a temperature dependent solid substrate preconcentrator.

9. A method according to claim 1, wherein analyzing said sulphur gases to determine the presence of buried sulphur mineralization is accomplished by gas chromatography.

10. A method according to claim 9, wherein said gas chromatography involves preconcentration of said sulphur gases.

11. A method according to claim 9, wherein said gas chromatography involves preconcentration of said sulphur gases at low temperature.

12. A method according to claims 10 and 8, wherein a sulphur specific flame photometric detector is utilized to analyze preconcentrated gases.

* * * * *